US 6,619,135 B2

(12) United States Patent
Liebemann et al.

(10) Patent No.: US 6,619,135 B2
(45) Date of Patent: Sep. 16, 2003

(54) FORCE SENSOR HAVING A SUBSTRATE FOR MEASURING DEFORMATION OF THE SUBSTRATE

(75) Inventors: Edwin Liebemann, Leonberg (DE); Dietmar Arndt, Kleinsachsenheim (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/971,747

(22) Filed: Oct. 5, 2001

(65) Prior Publication Data

US 2002/0104382 A1 Aug. 8, 2002

(30) Foreign Application Priority Data

Oct. 6, 2000 (DE) .......................................... 100 49 461

(51) Int. Cl.[7] .............................................. G01N 29/04
(52) U.S. Cl. ............... 73/801; 73/862.381; 73/862.391; 73/862.41
(58) Field of Search ............................ 73/801, 862.381, 73/862.391, 862.41, 862.59, 862.621, 152.16, 861.18, 861.25, 861.26; 177/210 R, 210 FP, 210 C, 211

(56) References Cited

U.S. PATENT DOCUMENTS 6,339,956 B1 * 1/2002 Huinink et al. .......... 152/152.1

* cited by examiner

Primary Examiner—Edward Lefkowitz
Assistant Examiner—Corey D. Mack
(74) Attorney, Agent, or Firm—Kenyon & Kenyon

(57) ABSTRACT

A force sensor having a substrate for measuring forces is provided, on which substrate a first path and a second path for travel of acoustic surface waves are arranged. The two paths are arranged essentially parallel to one another and their lengths are different. An effect of a force on the substrate is detectable by measuring a time needed for an acoustic surface wave to travel at least one of the first and second paths.

8 Claims, 6 Drawing Sheets

FORCE SENSOR HAVING A SUBSTRATE FOR MEASURING DEFORMATION OF THE SUBSTRATE

BACKGROUND INFORMATION

Force sensors measuring the deformation of a substrate using a path for an acoustic surface wave are known. When a force acts upon the substrate, the time needed by the acoustic surface wave to cover the path is changed.

SUMMARY OF THE INVENTION

The force sensor according to the present invention has the advantage over the related art that the effect of a force on the substrate can be detected in two directions perpendicular to one another. Thus different force components can be measured using a single sensor element.

A particularly simple embodiment of the path is represented by comb-shaped capacitor structures and barriers. A substrate made of a piezoelectric material is particularly easy to use here. The electric signals are advantageously transmitted and received via an antenna. The substrate is implemented in a particularly simple manner by a plate on whose top surface the first and second paths are implemented. Additional paths can be arranged on the bottom of the plate-shaped substrate in order to allow a force component to be measured in a third direction. The substrate can also be provided for embedding in an elastic material.

DETAILED DESCRIPTION

Figure 1:
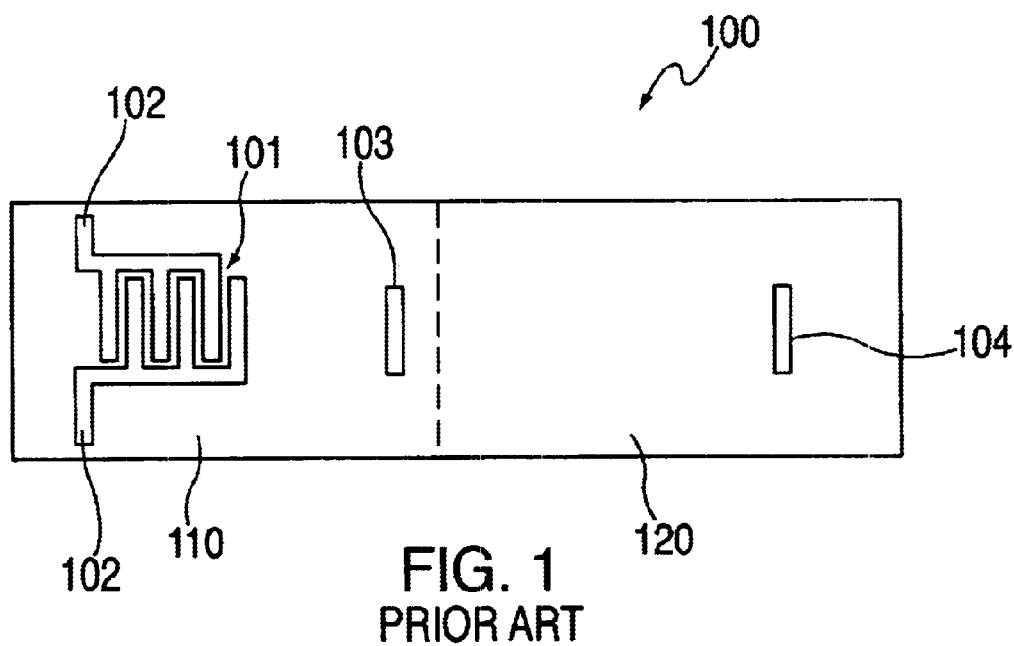
FIG. 1 shows a force sensor according to the related art.
Figure 2:
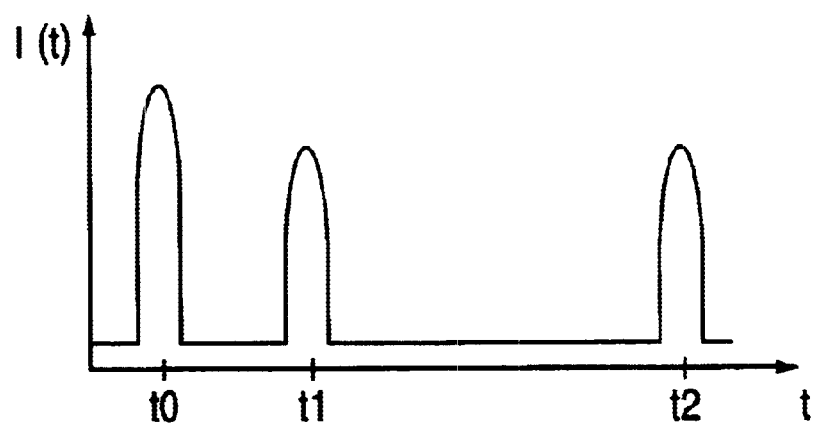
FIG. 2 shows the signals of the sensor according to FIG. 1.
Figure 3:
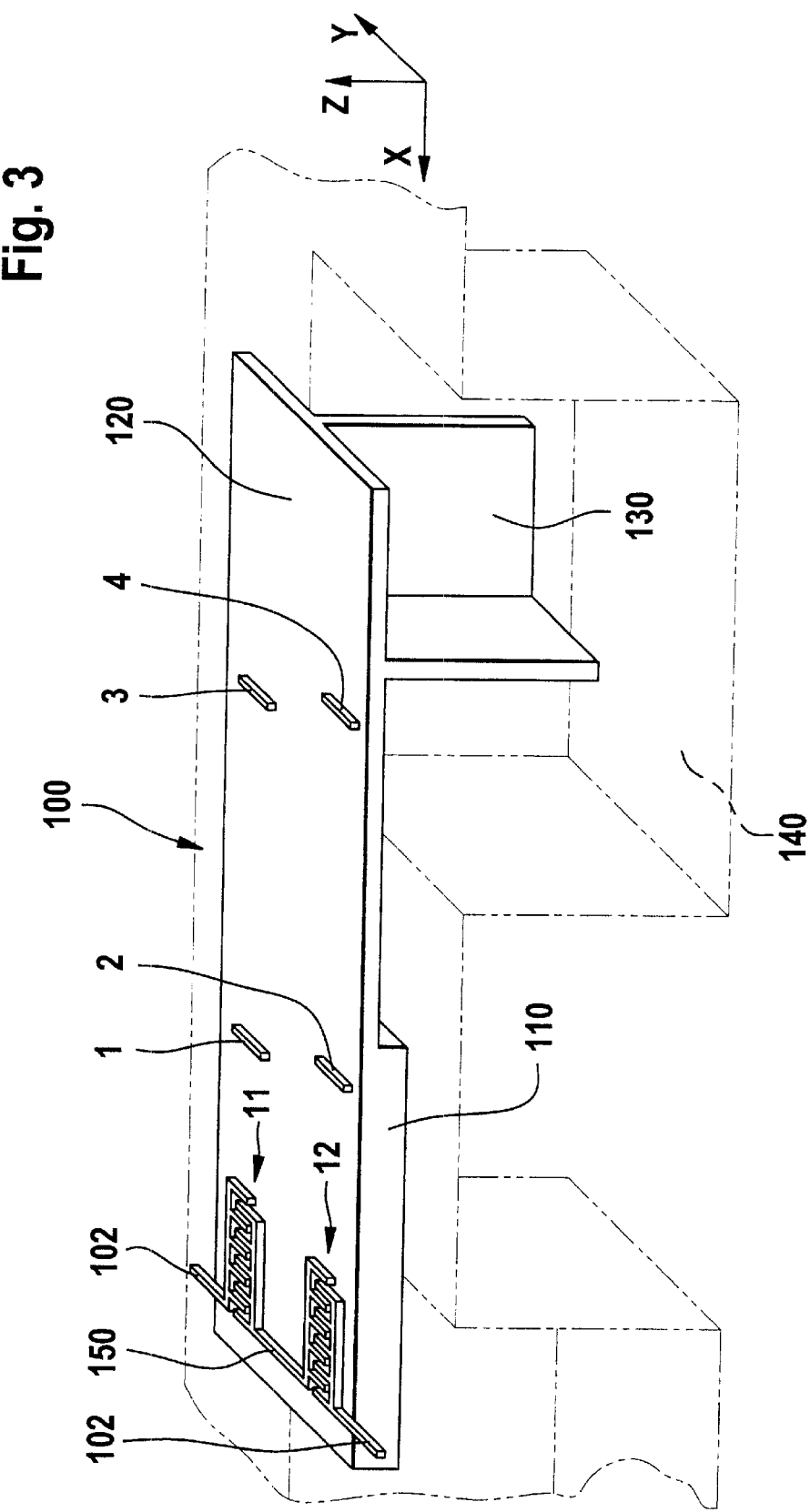
FIGS. 3, 4 and 5 show a first embodiment of the present invention with forces acting in different directions.

FIGS. 1 to 3 illustrate the basic principle of force sensors in which a path is provided for acoustic surface waves. FIG. 1 shows a top view onto a substrate 100, which is made of a piezoelectric material. A finger-shaped capacitor structure 101, implemented using thin-layer metal plating for example, is provided on the substrate, a plurality of individual capacitor fingers engaging with one another. When electric voltages are applied, the geometric distances between the individual fingers produce a deformation in the piezoelectric material of substrate 100, producing an acoustic surface wave in substrate 100. This is an acoustic surface wave, since it propagates in the material of substrate 100 with the speed of sound and is manifested through deformations of the surface of substrate 100. The deformations in the area of capacitor structure 101 arise due to the electric voltages applied, since the application of electric voltages causes piezoelectric materials to deform. In order to apply electric voltages to capacitor structure 101, an antenna arrangement 102 is provided, which is also implemented using thin-layer metal plating. Thus, if the antenna receives a high-frequency electric signal, the corresponding electric voltage is applied to capacitor structure 101 and an acoustic surface wave is generated in substrate 100.

As mentioned previously, this acoustic surface wave propagates on substrate 100 with the speed of sound. From the capacitor structure the acoustic surface wave propagates along the longitudinal direction of substrate 100 and encounters there a surface reflection barrier 103. One portion of the acoustic surface wave is reflected at this reflection barrier 103 and then travels back again from barrier 103 to capacitor structure 101. Another portion of the acoustic surface wave, however, propagates further and is reflected again on a second barrier 104. Thus, an acoustic surface wave returns from barrier 104 to capacitor structure 101 with a certain time offset. The acoustic surface waves reflected from barriers 103,104 produce corresponding deformations in the piezoelectric material beneath capacitor structures 101, which generate electric voltages in capacitor structure 101 due to the piezoelectric effect. These electric voltages are then beamed outward in the form of a high-frequency signal via antennas 102. Thus capacitor structure 101 and barriers 103, 104 form a path for acoustic surface waves.

FIG. 2 shows the intensity of high-frequency signals l(t) plotted against time t. At a point in time t0, a first strong high-frequency signal, representing the excitation signal, occurs. This signal is beamed in from outside and produces the acoustic surface wave in capacitor structure 101 of substrate 100. At time t1, a high-frequency signal, triggered by the surface wave reflected at barrier 103, is transmitted by antennas 102. At time t2, a second high-frequency signal, triggered by the surface wave reflected at barrier 104, is transmitted by antennas 102.

The intervals of the signals at times t1 and t2 with respect to time t0 and between one another provide information regarding substrate 100, since these time differences depend on the propagation time of the acoustic surface waves in substrate 100. The propagation time of the acoustic surface wave in substrate 100 is influenced, for example, by the temperature of substrate 100. Furthermore, the propagation time is influenced by mechanical deformations of substrate 100. In order to separate these effects from one another, in FIG. 1 substrate 100 has a rigid area 110 and a flexible area 120. Rigid area 110 in particular may be thicker than flexible area 120. Thus, when a mechanical force is applied to substrate 100 at the end of substrate 100 facing away from capacitor structure 101, substrate 100 will bend predominantly in flexible area 120. This is manifested in the propagation time of the acoustic surface wave in flexible area 120, so that time t2 is shifted with respect to time t0. Since barrier 103 is arranged in the mechanically stable area 110, time t1 is not shifted with respect to time t0 in first approximation, even if a mechanical force is applied. Thus the propagation time of the surface wave depends only on the temperature in this area. The interval measured between times t0 and t1 therefore provides information on the temperature of substrate 100. The time differences measured between times t0 and t2 provide information regarding the force applied to substrate 100.

The device according to FIG. 1 is therefore well suited as a force sensor through which a force acting on substrate 100 can be detected. The time shift of the signal reflected from barrier 104 is influenced by both the force applied and the temperature of the substrate. The influence of the temperature on this signal, however, can be eliminated by taking into account the signal reflected by barrier 103.

Thus a path for acoustic surface waves on piezoelectric substrate 100 is implemented by finger-type capacitor structure 101 and barriers 103, 104. Other possibilities of implementing such a path on a piezoelectric substrate 100 are also possible. For example, two capacitor structures can be applied to the substrate, one of which is designed to excite acoustic surface waves and the other to receive acoustic surface waves. The propagation time of this signal would then also be influenced by the mechanical stresses in the substrate. If other possibilities are available for measuring the temperature of substrate 100, barrier 103 according to FIG. 1, for example, is not needed, since this barrier mainly supplies temperature information.

An element such as illustrated in FIG. 1 is, however, only capable of measuring a single force component that is perpendicular to the substrate. In the following figures, a force sensor according to the present invention is described, through which a plurality of force components which are perpendicular to one another can be detected.

FIG. 3 shows a piezoelectric substrate 100 on which a first finger-type capacitor structure 11 and a second finger-type capacitor structure 12 are arranged. First finger-type capacitor structure 11, together with barriers 1 and 3, which are also arranged on substrate 100, forms a first path for acoustic surface waves. Furthermore, a second finger-type capacitor structure 12 is provided on substrate 100 which, together with barriers 2 and 4 on substrate 100, forms a second path for acoustic surface waves. Substrate 100 has a first rigid area 110, first and second capacitor structures 11, 12, and barriers 1, 2 being arranged in this first area. Furthermore, substrate 100 has a flexible area 120, on which barriers 3 and 4 are arranged. On the bottom of the thinner area 120, a force introduction element 130 is also arranged. Substrate 100 and force introduction element 130 are embedded in an elastic material such as the rubber of an automobile tire, for example. This elastic material, in which substrate 100 is embedded, is not illustrated in FIG. 3. However, the outer limits 140 of this elastic material are shown for the sake of clarity. This can be an automobile tire in particular, i.e., outer limit 140 is represented by the profile of such a tire. First and second capacitor structures 11, 12 are electrically connected together via a connecting web 150. Furthermore, these structures are electrically connected to antenna elements 102, through which in turn a high-frequency signal can be introduced from the outside and/or a corresponding signal can be emitted as a function of electric voltages in capacitor structures 11, 12.

FIG. 3 shows substrate 100 when no forces are acting on the embedding elastic material. The electric signals generated in this state when a high-frequency signal is introduced are illustrated in FIG. 6.

Figure 6:
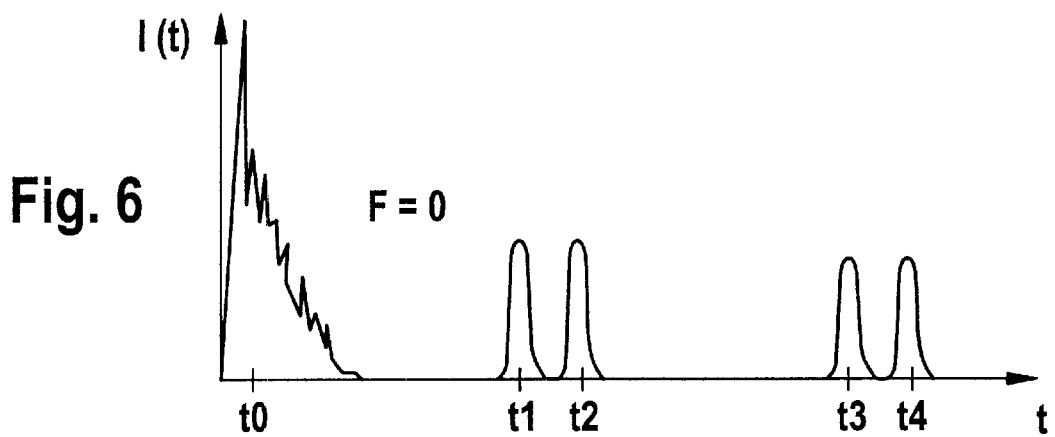
FIGS. 6, 7 and 8 show the signals of the sensors according to FIGS. 3, 4, and 5.

FIG. 6 shows the intensity of a high-frequency signal l(t) plotted against time t. At time t0, excitation occurs by the introduction of an external high-frequency pulse, which excites both first capacitor structure 11 and second capacitor structure 12, so that they emit acoustic surface waves. At time t1, the surface waves reflected at barrier 1 arrive at first capacitor structure 11 and a corresponding high-frequency signal is emitted via antennas 1 and 2. At time t2, the surface wave reflected at barrier 2 arrives at second capacitor structure 12, and a corresponding signal is emitted again. In order to easily separate these two pulses, barriers 1 and 2 are arranged with an offset with respect to the propagation distance to the respective capacitor structures. Barrier structures 3 and 4 are also arranged with an offset with respect to one another, so that at time t3, the surface wave reflected by barrier 3 arrives at first capacitor structure 11 and at time t4 the surface wave reflected by barrier 4 arrives at second capacitor structure 12.

Figure 4:
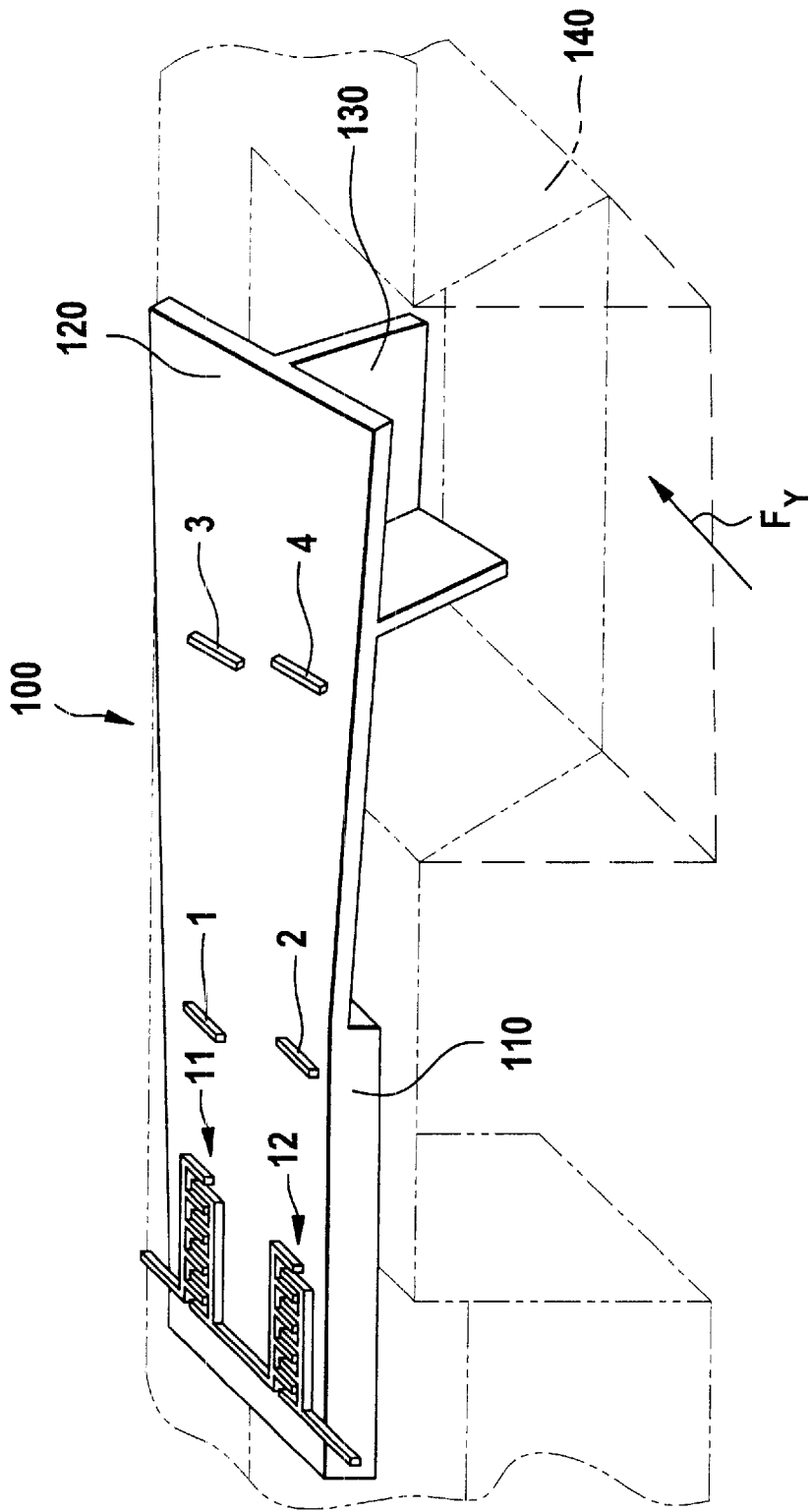

FIG. 4 shows the force sensor when a force is applied in the Y direction (the coordinate system is illustrated in FIG. 3). Objects that are identical to those of FIG. 3 are identified with the same symbols. The force in the Y direction causes the elastic medium in which substrate 100 is embedded to deform, as illustrated by a corresponding shift of surface 100 of the elastic mass. Force introduction element 130 causes substrate 100 to twist correspondingly. This twisting acts predominantly on flexible part 120 of substrate 100 since this part has a reduced thickness and is therefore more flexible. The thicker rigid area 110 of substrate 100 is, however, only slightly deformed.

Figure 7:
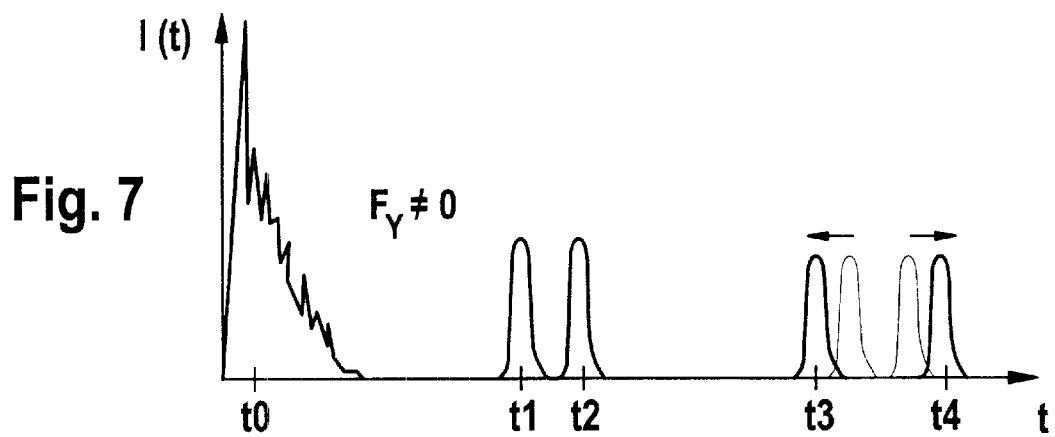

FIG. 7 shows the change in intensity signals l(t) due to the effect of the force in the Y direction against time t. The signals at times t0, t1, and t2 correspond to the signals as illustrated in FIG. 6. This is due to the fact that there is no deformation in area 110 of substrate 100, and thus no change in the signals generated there. As FIG. 7 clearly shows, however, twisting of area 120 of substrate 100 causes times t3 and t4, i.e., the times when the reflected signals arrive from barriers 3 and 4, to shift noticeably. FIG. 7 shows again the signals at times t3 and t4 of FIG. 6 in fine lines, while the shifted signals are shown in thick lines. As FIG. 7 shows, time t3 is shifted with respect to FIG. 6 to an earlier point in time, while time t4 is shifted to a later point in time. This is also illustrated by the arrows in FIG. 7. Thus, the force in the Y direction shortens the propagation time in the first path, formed by capacitor structure 11 and barrier 3, and lengthens it in the second path formed by capacitor structure 11 and barrier 4.

Figure 5:
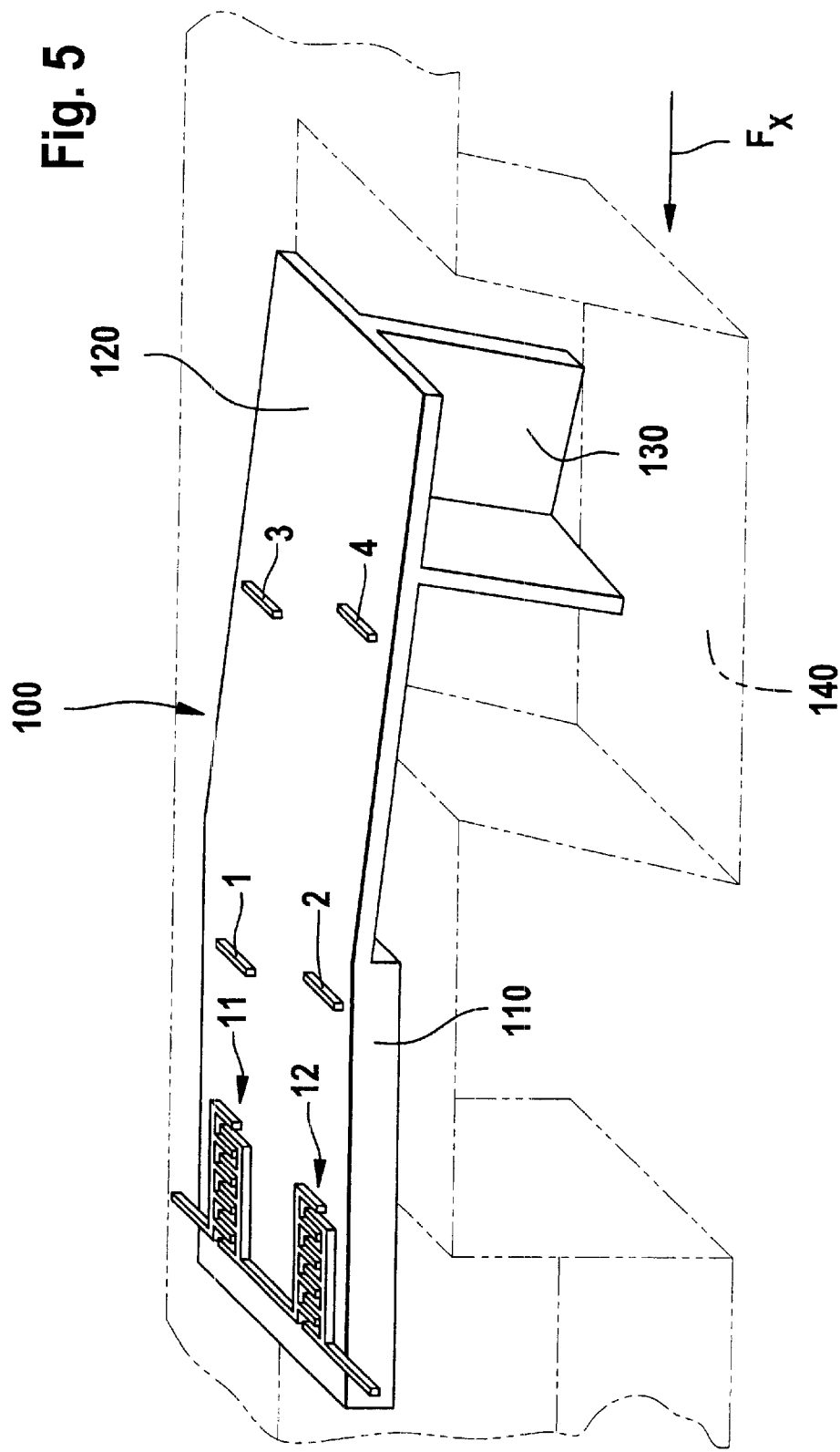
Figure 8:
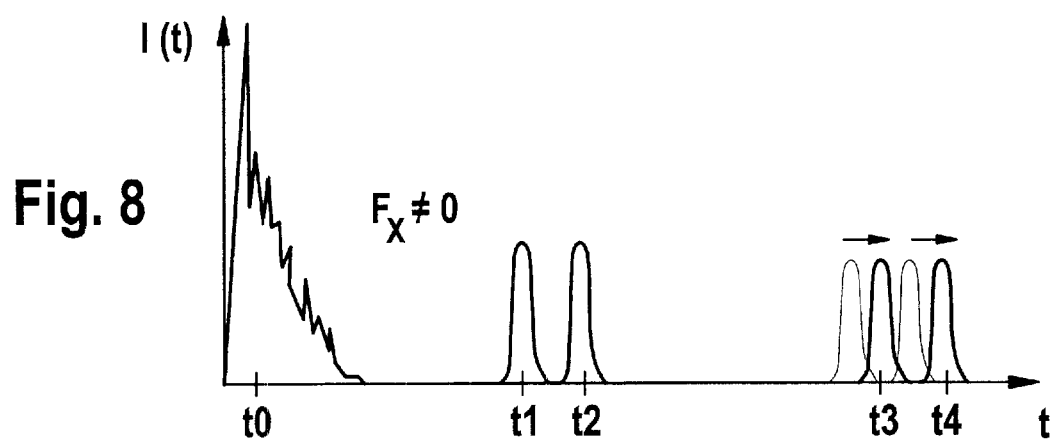

FIG. 5 shows the effect of a force in the X direction. The same objects are again identified with the same symbols as in FIGS. 3 and 4. As can be seen in FIG. 5, a force in the X direction basically deforms deformable area 120 of substrate 100. Since the force in the X direction basically only bends flexible area 120 downward in the negative Z direction, the effect on the signal propagation times is basically the same in both paths. This can also be seen from FIG. 8, in which the signals when a force is introduced in the X direction are illustrated in a manner similar to FIGS. 6 and 7. The signals at times t0, t1, and t2 again correspond to FIGS. 6 and 7. The signals at times t3 and t4 are drawn in thick lines, and the original signals at times t3 and t4 according to FIG. 6 are drawn in fine lines. As the arrows also show, both times t3 and t4 are shifted with respect to no-stress times t3 and t4 of FIG. 6 to a later point in time.

Thus, the effects of forces in the X and Y directions can be clearly separated using the two paths on substrate 100. The two paths running parallel on substrate 100 thus allow the two force components to be detected simultaneously.

Figure 9:
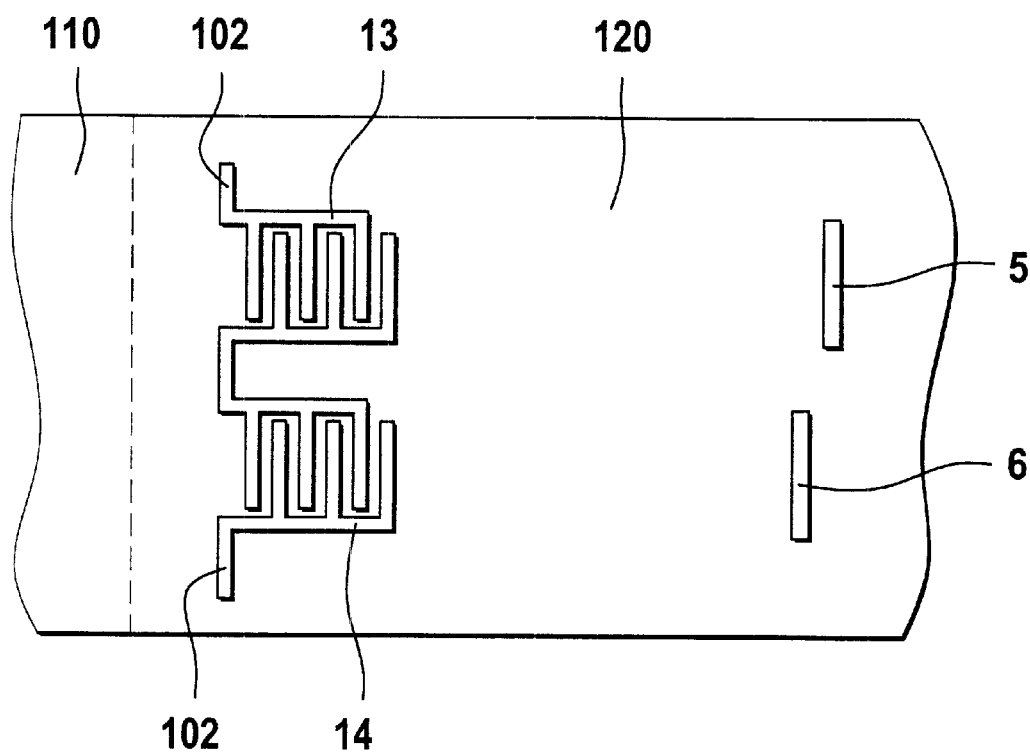
FIG. 9 shows an additional embodiment of the present invention.

FIG. 9 shows another embodiment of the present invention. FIG. 9 shows a bottom view of substrate 100. The top view of this substrate 100 corresponds to FIGS. 3 through 5, i.e., the first and second paths are arranged on the top side of this substrate as shown in FIGS. 3 to 5. Two additional paths, shown in FIG. 9 by the bottom view onto partial areas 110 and 120, are arranged on the bottom side of the substrate. A third and a fourth comb-shaped capacitor structure 13 and 14, which together with the respective barriers 5 and 6 form two additional paths, are provided on the bottom side of area 120. The two comb-shaped capacitor structures 13 and 14 are again connected to antennas 102 for reception and transmission of high-frequency signals.

The signals of paths 3 and 4 arranged on the bottom side allow an additional force in the Z direction to be detected. As in the case of a force acting in the X direction, a force in the Z direction causes flexible area 120 of substrate 100 to bend. In the case of a force in the X direction, not only does area 120 bend, but a force component also acts directly on substrate 100 in the X direction, influencing the propagation time of the surface waves in substrate 100. However, a force in the Z axis direction, only causes area 120 to bend. Therefore, in first approximation, the effect of a force in the Z direction is the same on the top and bottom of substrate 100, but with different signs. In the case of a force introduced directly in substrate 100 in the X direction, the effects on the propagation time of the surface waves on the top and bottom sides are also of opposite signs, but their absolute values are not equal. Thus a distinction can be made between the effect of a force in the X direction and of a force in the Z direction.

What is claimed is:

1. A force sensor comprising:
   a substrate; and
   a first path and a second path provided on the substrate for acoustic surface waves, the first and second paths being substantially non-overlapping and parallel to one another, the first path having a different length than the second path;
   wherein an effect of a force on the substrate is detectable by measuring a time needed for an acoustic surface wave to travel at least one of the first and second paths.

2. The force sensor according to claim 1, wherein the first and second paths include an arrangement of comb-shaped capacitor structures on a piezoelectric material and an arrangement of reflection barriers on the substrate.

3. The force sensor according to claim 2, wherein the substrate is composed of a piezoelectric material and the capacitor structures are directly applied to a surface of the substrate.

4. The force sensor according to claim 2, further comprising antenna elements connected to the capacitor structures.

5. The force sensor according to claim 2, wherein the substrate is a plate-shaped substrate, and the first and second paths are situated on a top side of the plate-shaped substrate.

6. The force sensor according to claim 5, further comprising at least one additional path situated on a bottom side of the plate-shaped substrate.

7. The force sensor according to claim 1, wherein the substrate is embedded in a deformable medium.

8. The force sensor according to claim 7, wherein the deformable medium is a material of an automobile tire.

\* \* \* \* \*